United States Patent [19]

House

[11] 4,255,023
[45] Mar. 10, 1981

[54] OBJECTIVE RETINAL RESPONSE RECORDER

[76] Inventor: Harold D. House, Suite 1010, Kelly Prof. Bldg., 6565 S. Yale, Tulsa, Okla. 74136

[21] Appl. No.: 11,375

[22] Filed: Feb. 12, 1979

[51] Int. Cl.$^3$ .............................................. A61B 3/06
[52] U.S. Cl. ....................................... 351/24; 351/36
[58] Field of Search ................ 351/24, 39, 23; 351/36

[56] References Cited

U.S. PATENT DOCUMENTS

| | | | |
|---|---|---|---|
| 3,421,498 | 1/1969 | Gans | 351/24 X |
| 3,883,235 | 5/1975 | Lynn et al. | 351/39 |

OTHER PUBLICATIONS

*Design*, "On the Line of Sight", pp.24-31, Apr. 1959.

*Primary Examiner*—Paul A. Sacher
*Attorney, Agent, or Firm*—Head & Johnson

[57] ABSTRACT

A retinal response recorder that is fully automatic, comprises a light stimulator, with means for a patient to position his head, such that his eye is on the horizontal axis of the stimulator. Means are provided for selecting any one of the selected number of light beams directed from the stimulator to the eye of the patient at selected angular positions above and below the horizontal and left to right of the vertical plane through the axis of the stimulator. Appropriate electrodes are positioned on the skin surface of the patient to record electro-muscular potentials generated by the retina of the eye. Means are provided for a prearranged program of selection of stimulator spots. If the eye sees the spot of light a retinal response potential is generated and/or a visually evoked response is generated. These signals, one or both, go to amplifiers with selected filter characteristics, and then to a display-recorder apparatus, so that the magnitude of the response can be determined with regard to the specific position of the spot of light.

15 Claims, 9 Drawing Figures

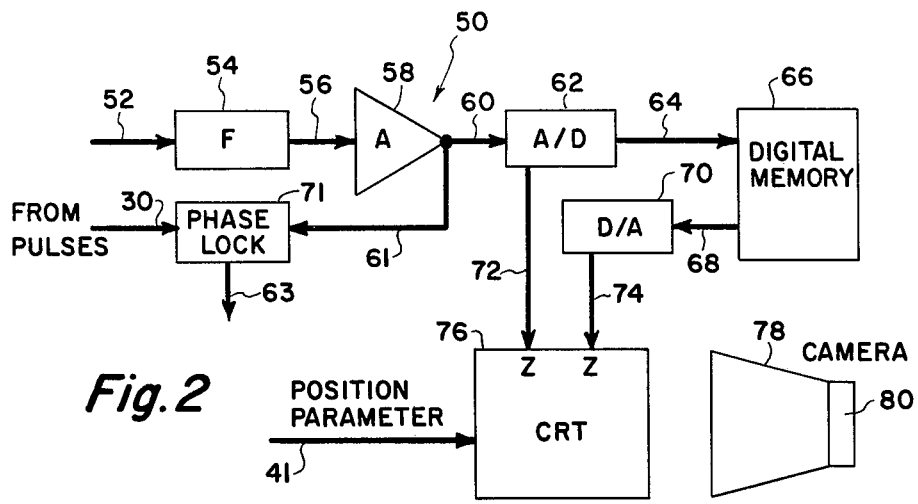
*Fig. 2*
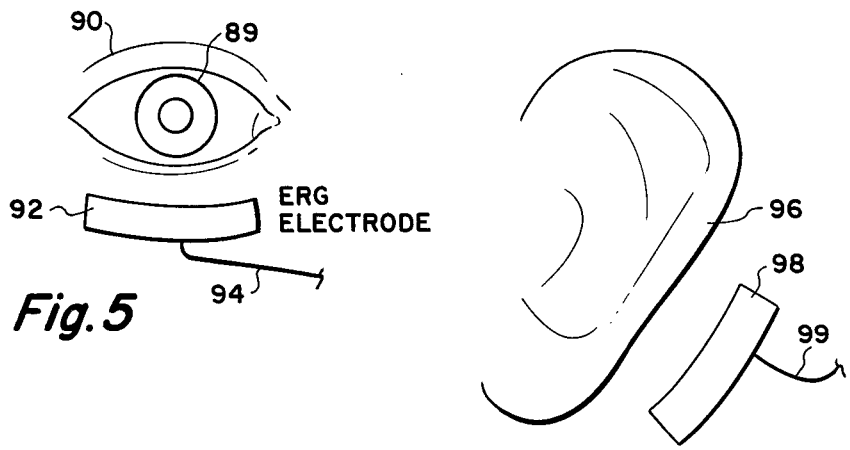
*Fig. 5*
*Fig. 6*
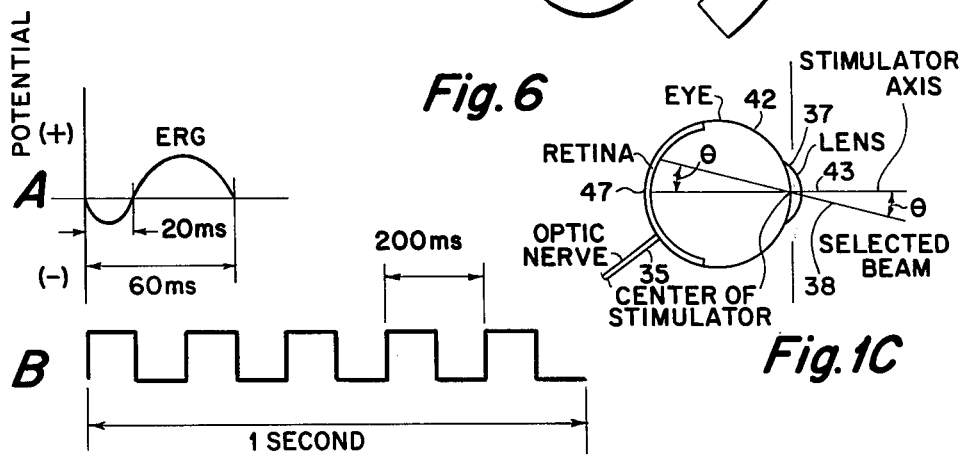
*Fig. 7*
*Fig. 1C*

OBJECTIVE RETINAL RESPONSE RECORDER

BACKGROUND OF THE INVENTION

1. Field of the Invention

This invention lies in the field of study of the human eye. More particularly it concerns a process of determining the physiological condition of the retina of the eye, and of measuring the field of vision of the eye, by entirely objective automatic means irrespective of arbitrary eye movements of the patient.

2. Description of the Prior Art

In the prior art, ophthalmologists have routinely made measurements on the eyes of patients, such as determining the visual field by seating a patient before a blackened board and have a test person move a small whitened sphere along radial lines from the outer extreme of the board toward the central portion, in such a manner that the patient responds when he sees the spot, being cautioned to maintain the eye constantly fixed along the axis of the board. In other cases, semiautomatic stimulators have been used in which a plurality of small lamps are positioned at selected locations on a board or hemisphere. These lights are illuminated momentarily in selected succession and the patient indicates by closing a switch or pressing a button that he does or does not see the spot of light.

Also in the study of the visual process, research personnel have made measurements of the potential generated by the retina in response to a visual stimulus. These measurements have been made at various positions on the face and forehead of the patient by means of thin metal electrodes which are attached to the skin surface.

There are two particular types of potentials which are measured, namely, the electro-retinal potential and the visual evoked response.

These and other measurements can be made on the apparatus of this invention by the use of suitably placed electrodes, as are well known in the art.

SUMMARY OF THE INVENTION

It is the primary object of this invention to provide an electronic apparatus which is fully automatic, and on a prearranged program can provide any one of a plurality of separate light beams projected into the eye of the patient, at selected angles, with appropriate measurements being made of the visual evoked response (VER), and the electro-retinal potential (ERP), or other types of electrical measurements, which in one way or another may be responsive to the process of recognition by the eye and the brain of the optical stimuli.

It is a further object of this invention to provide means to digitize and make amplitude measurements on these potentials, and to display these potentials as a function of angular position of the stimulus spot with respect to the axis of the stimulator and to the axis of the eye so that a record may be made for future comparison.

These and other objects are realized and the limitations of the prior art are overcome in this invention by providing an apparatus which includes specific elements, including an optical spot stimulator, an eye fixation monitor, a spot control memory means which can produce a series of address locations which can be selected sequentially, or at random, to mark the location of successive light stimuli, In response to the output of the spot control memory, a selection is made in a stimulus selector of an individual electric lamp, or optical beam, at the selected angle with respect to the axis of the stimulator, and the optical axis of the eye of the patient.

By means of the eye fixation monitor and the crossed pairs of photocells, even though the eye of the patient may wander from the optical axis of the stimulator, the actual position of the eye in angular coordinates, or other incremental measurements, can be observed, and the selection of the beams from the stimulator can be modified so that the actual position of the beam in the stimulator is modified by the differential movement of the eye, as observed by the fixation monitor, so that the direction of passage of the light beam through the lens to the retina will be in the precisely desired direction. Several types of automatically positioned light beams will be described.

Means are provided to take the potentials observed on the electrodes attached to the surface of the skin, and to filter, amplify, determine the amplitude of the response, digitize the wave shape of the response if desired, and to display on a cathode ray tube or other display/record means at a position which corresponds to the angular or rectangular position of the beam of the stimulator. Conventional means are provided for placing a camera and camera hood, over the cathode ray tube, in order to record the positions of the spots, and some parameter of the response to the light, at those specific locations.

BRIEF DESCRIPTION OF THE DRAWINGS

These and other objects and advantages of this invention and a better understanding of the principles and details of the invention will be evident from the following description taken in conjunction with the appended drawings in which:

FIGS. 1A, 1B and 1C illustrate further details of the stimulator.

FIG. 2 illustrates in block diagram form the amplifying, processing, and display features of one embodiment of this invention.

FIGS. 5 and 6 illustrate two methods of applying electrodes for measuring the evoked potentials.

FIG. 7 illustrates a manner in which the stimulated light beam can be modulated to provide an improved potential response curve for the ERG.

DESCRIPTION OF THE PREFERRED EMBODIMENT

Figure 1:
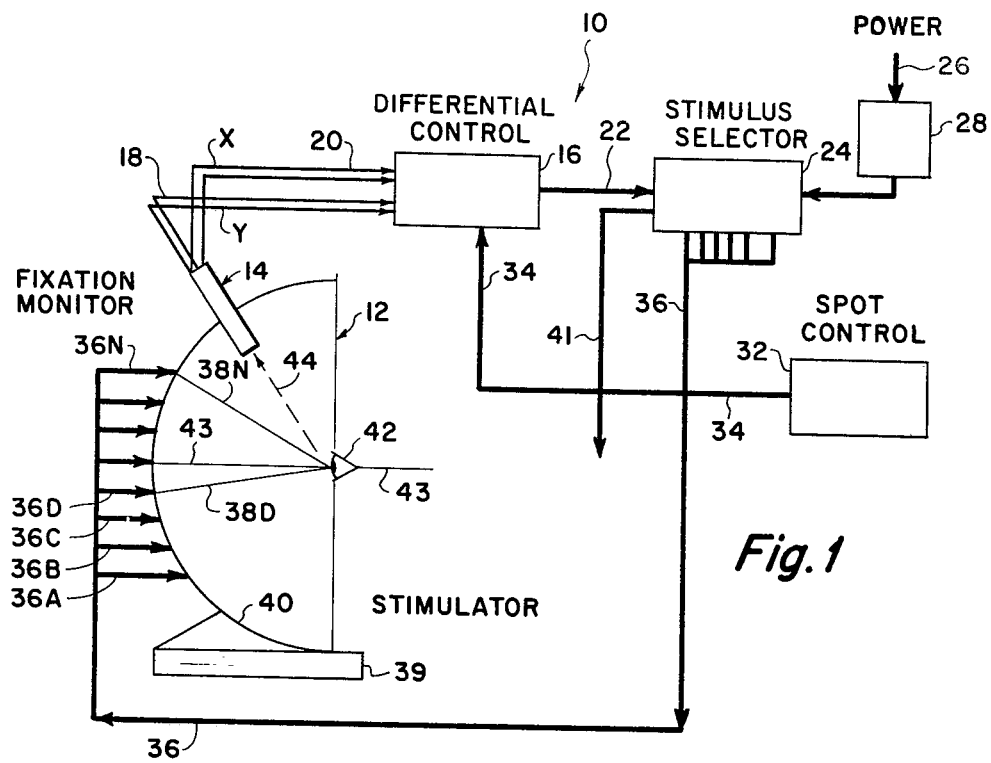
FIG. 1 represents in block diagram form, one embodiment of an apparatus for stimulating the eye of a patient with a preselected sequence of angular beams.

Referring now to the drawings and in particular to FIGS. 1, 1A, 1B and 1C, there is illustrated in FIG. 1C a simple model of the eye indicated by the numeral 42, with a lens 37 on the front of the eyeball and a retina 47 which covers a selected angular area of the back inside wall of the eye. An optic nerve 35 departs from the eyeball and the retina at a selected angle. The horizontal axis of the eye and of the stimulator is indicated by the numeral 43. A selected stimulator light beam 38 is shown at an angle to the optical axis of the stimulator and of the eye.

In the testing of the retina it is important that the condition of the eye at each small area of the retina must be measured separately from each of the other areas.

Thus the eye must be held as closely as possible at a position so that the eye is on the axis of the stimulator, and the axis of the eye is directed constantly to the point of intersection of this axis and the wall of the stimulator. If the eye can be maintained in that position, then as different light beams are produced at known angles to the axis 43, then the exact position of the inpingement of the light beam on the retina is also known and the response can be plotted as a function of the coordinates of the retina.

However, it is difficult for a patient to maintain the eye beam directed constantly at the axis of the stimulator, and there is a tendency for it to move up or down, or sideways, through some small angle. This variability of the position of the eye is determined by measurement on the eye, by means of a fixation monitor. The output reading of that monitor in terms of a voltage, which is a function of the angular movement of the eye away from axis 43 is then used to correct the selected position of the beam being generated by the stimulator, so that the point of impingement of the light beam on the retina will be the prescribed angle, that the beam would have reached if the eye had not wandered from the axis of the stimulator.

FIG. 1 illustrates schmetically the apparatus that produces the desired optical beams in a selected sequence. One type of stimulator is shown in FIG. 1. This has a hemispherical shell, indicated generally by the numeral 12, the spherical surface 40 is blackened inside, and has a plurality of small openings 45 (FIG. 1A) through the wall, into which appropriate small lamps 46 can be inserted. The diameter of the hole and of the lamp is such that the angle subtended at the center of the hemisphere will be one second of arc. Thus the corresponding lighted area of the retina likewise will be one second of an arc, which has been selected as a standard unit area for examination of the retina.

There are a network of conductors 36A, 36B, 36C... 36N which are carried, and the lines 36, from a stimulus selector 24, which will be described in detail later. A spot control memory 32 comprises a paper tape reader, or equivalent memory source, such that by selecively moving from one address to another, the coordinates of the selected lamp attached to the wires 36 will be chosen by the stimulus selector 24, in response to the address provided over leads 34 from the spot control memory. The selector 24 will switch in the proper lamp 36A over the leads 36 so that a beam will then originate from the lamp, say 36D for sample, to the eye 42 positioned on the axis 43 of the hemisphere 40.

Appropriate means may be provided on the stimulator 40 such as resting the chin on an adjustable support, and holding the head in a specified position so that the beam which is relatively narrow in breadth, will pass through the center of the lens of the eye, at the proper angle, and on to the retina.

The fixation monitor 14 is a commercial device which comprises a microscope, which receives light from the eye over dashed line 44, and magnifies the image of the eye. By means of two pairs of crossed photocells it can determine the movement of the eye, over a selected angular range. The output of the fixation monitor is provided by two pairs of leads 18 and 20 which represent, for example, the Y axis movement and the X axis movement of the eye relative to the axis 43 of the stimulator and of the eye.

The output of the spot control memory 32, for any given address may be in any desired form. In one form it can be two voltages, an X voltage and a Y voltage. These go by lead 34 to a differential control 16. There are means for adding to the X and Y values on line 34, the X' and Y' values on lines 20 and 18, in a proper algebraic manner, to provide an output signal on leads 22, which provide the sum of the two values of $X+X'=X''$ and $Y+Y'=Y''$. This controls a stimulus selector to move or switch to another spot, such that the position of the image of the light spot on the retina will be at the true angular position X and Y desired.

Power for the output of the stimulator, that is, power to the lamps on leads 36, is provided over leads 26, and may for example go through a pulser switch 28, and through leads 30 to the selector. The purpose of the pulser 28 is to provide a sequence of pulses such as shown for example in Part B of FIG. 7, where a sequence of five or more square wave pulses of light are provided, each pulse of light say 100 milliseconds in duration, for example, and each space another 100 milliseconds. Thus the whole sequence may operate for a second or for several seconds. It is then possible to determine from the received signal what the component of signal there may be that has a periodicity, or frequency, equal to that of the imposed light pulsations. That portion of the signal picked up at the electrodes on the skin of the patient, which has this desired periodicity, can then be verified as a true signal, which is responsive to the light generated by the stimulator, and not a noise.

Figure 1A:
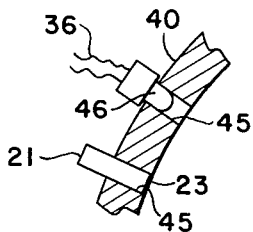

Referring now to FIG. 1A there is shown a small portion of the wall 40 of the hemisphere stimulator, and a pair of openings 45 of selected diameter drilled through the wall. In one of them, a lamp 46 is inserted which is supplied with current by leads 36. The diameter of the opening 45 is such that at the radius of the sphere 40, is subtends at angle of 1°.

Figure 1B:
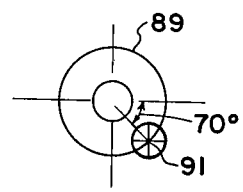

In FIG. 1B is shown a portion of the eye in which the iris and the shaded portion of the eye, known as the limbus are shown. There is a circumferential line 89 marking the outer edge of the limbus against the white area of the eye. At a point on the perimeter 89 which is approximately 70° down from the horizontal the fixation monitor is focused with the cross-hairs, or crossed photocells 91 positioned with their axes horizontal and vertical. As they eye moves and the edge of the limbus 89 moves up or down or sideways, voltages will be generated in the photocells such that on the leads 18 and 20 they will represent the actual displacement in the X and Y directions with reference to the point 91, the point of fixation of the monitor.

While there are many ways in which the stimulator can be built one of these has been shown in FIG. 1 which comprises a plurality of separate lamps, which are switched in, sequentially. These lamps are positioned in a grid, of selected design, either measured in angle radiating out from the axis, and angles of rotation between vertical and horizontal, for example, or they can be positioned in a selected rectangular grid of any desired spacing, for example.

Figure 4:
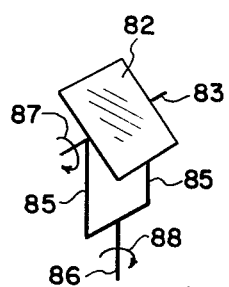
FIG. 4 illustrates a detail of FIG. 3.
Figure 3:
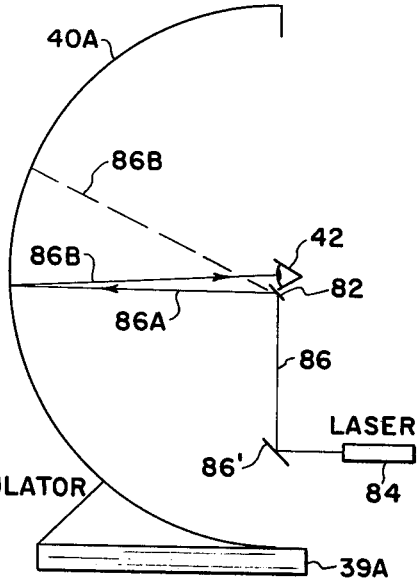
FIG. 3 illustrates an alternative design of stimulator.

Shown in FIGS. 3 and 4 is another embodiment in which the stimulator can be a hemisphere 40A, as compared to the hemisphere 40 in FIG. 1. At the position just below the eye, is a mirror 82 which receives light from a laser 84 of, selected intensity, which goes by way of mirror 86' and beam 86, to the mirror 82 and then by beam 86A to the wall of the hemisphere 40A, where it impinges upon a metal plug 21 (FIG. 1A) inserted into the opening 45. The front face 23 of the plug is a brightly polished metal surface, which reflects the light backwardly to the eye 42 of the patient. In other words by rotating the mirror in azimuth and elevation, the light beam 86A can be made to contact any one of the plurality of plugs 21, at fixed desired locations in the shell 40A and the light will then be reflected back to the eye at substantially the desired angle.

By referring to FIG. 4 there is shown schematically a type of small mirror 82 that has a horizontal axis 83 that can rotate in the direction of arrow 87. The axis 83 is supported in a yoke with two upright arms 85 and a central vertical arm 86, which is set in bearings (not shown) such that it can rotate the entire assembly in accordance with arrow 88. Thus by driving the mirror and the yoke about the two axes 83 and 86, by selected angular increments such as by step motors or servo motors, for example, in the well known manner, the beam can be positioned to any selected angle in azimuth or in elevation, with respect to the axis 43 of the hemisphere.

As previously stated, the apparatus consists of two essential parts. The first is an apparatus for producing a spot of light at a selected location on the wall of a hemisphere, for example, at selected angular location with respect to the axis of an eye positioned at the center of the hemisphere. This can be accomplished in many ways.

The feature that is very important in an automatic machine is to provide the fixation monitor 14 to provide adequate signs for the measurement of any deviation of the axis of the eye from the axis of the stimulator, so that the position of the light spot can be varied, such that with the known displacement of the eye the resultant angle of the image of the spot on the retina will be at the desired angular position, irrespective of how much the eye has drifted from its proper axial direction.

In order to make this apparatus fully objective and automatic it remains then to provide a means for generating a potential which is a function of the reception of the light spot signal to the retina, and to amplify and process this signal, to determine its validity, that is, to determine whether that signal is due to the light spot of the stimulator or is due to some other noise source, and so on. One way of determining the validity of the signal, as has been discussed, is by using a pulsating light spot and to search in the produced evoked response for that frequency of signal, and to display and record that particular component of the signal, the understanding being that any other electrical signal is a noise and should be disregarded.

Referring now to FIG. 2 there is shown one type of detecting and processing apparatus. This comprises an input lead 52 from one or another of a group of electrodes, which can be attached to the face and head of the patient. The purpose of amplifying and processing the signal, is to infer from the character of that potential, what the condition of the retina is, and what physiological problems may be present in the retina, the optic nerve or the brain for example. As will be explained in connection with FIGS. 5 and 6 there are a number of possible positions to place electrodes, and the potential of these electrodes will arrive on lead 52 from the electrode.

The received signal may pass through a filter 54 of selected band pass. The filter can of course be equivalent to a phase lock means 71 driven by the pulsing frequency of the current 28 that powers the light spot, or any other filtering apparatus. The filtered signal then goes by line 56 to a high-gain, low-noise amplifier 58, of which a number of examples are available on the market. These would be the equivalent of electroencephalograph type amplifiers, and so on. The amplified output then may go to an analog to digital (A/D) converter 62, where the particular wave shape of the evoked potential is digitized, and is stored in a digital memory 66.

Reference is made to part A of FIG. 7 where there is shown a sample wave shape representing the electro-retinal potential, which occurs whenever a light is suddenly received on the retina. This wave form lasts about 60 milliseconds, and then drops to 0, and remains at 0 even though the light stimulus may still be on the eye. Such a wave form as this would be digitized, and of course its amplitude thereby determined, and its wave shape stored in the digital memory 66. This can always be withdrawn from the memory over lead 68 to a digital-to-analog (D/A) converter 70, and then over lead 74, can be displayed on a cathode ray tube, as is well known in the art. Alternatively the potential brought in on lead 52 and after amplification delivered on lead 60, can then be brought over lead 72 to the cathode ray tube. These would go to the Z axis of the tube in order to produce a spot of a selected brilliance, which would be some function of the observed voltage, for example, as might be the case for a visual evoked response measurement (VER) of the eye.

The cathode ray tube 76 would have input on leads 41 corresponding to the angular position of the light spot in the stimulus selector 24, so that the spot which is presented on the cathode ray tube will be positioned at the coordinates X and Y in accordance with the precise angular position of the image of the spot on the retina of the patient.

The type of amplifying, filtering, processing and display apparatus illustrated in FIG. 2 is only by way of example, and other equivalent types of display can, of course, be utilized. The particular display apparatus also will vary with the type of coordinates of the stimulus light beams, whether generated by the lamps as in FIG. 1 or by the laser beam in FIG. 3. Of course, if a different type of stimulator, with a plane board is used as the surface, then some combination of rectangular and polar coordinates may be required. As is well known, a camera 80 with a hood 78 placed over the cathode ray tube 76, can be used for making a permanent record of the response of the eye at each of the stimulus positions.

Also shown in FIG. 2 is a lead 61 taken from the amplifier 58 and a corresponding lead 30 from the pulser 28 of FIG. 1, to a phase lock device 71, such that an output on lead 63 would indicate that the evoked response shows the pulsation frequency of the light stimulus provided, which would be verification that the measurement is a valid measurement of the eye.

In FIGS. 5 and 6 are shown two of many ways in which electrodes can be attached to the skin of the patient, on the face, forehead or scalp, in order to detect electrical potentials, which can be proven to be functions of the response of the retina, or optic nerve, or of the brain, in the processing of electrical signals from the retina. The ERG, or electro-retinal potential, it has been found, can be picked up readily by means of a thin metal plating on a flexible strip of plastic 92, to which is attached a silver wire lead 94, which goes to the line 52 of FIG. 2. This strip 92 is attached to the skin surface by means of adhesive tape placed over it in a manner similar to that by which electrodes are attached to the scalp for purposes of EEG measurement, for example. They are placed just below the lower lid of the eye 90 shown in FIG. 5. They can be placed at other positions also.

The VER potential or visual evoked response potential, can be detected by means of a similar silvered plastic strip 98 FIG. 6, which is positioned on the bony structure immediately behind the lower part of the ear. This potential is taken off by means of a silver wire 99, for example, to lead 52. The art of positioning these electrodes forms no part of this invention, and is well known in the art of medical testing.

Not shown but well known in the art is the manner in which electrodes may be attached to the scalp to indicate the response of certain areas of the brain, and in the same way that the ERG and VER potentials are utilized, the potential generated on the scalp electrodes can likewise be used for the same purpose.

Whereas, the present invention has been described in particular relation to the drawings attached hereto, other and further modifications apart from those shown or suggested herein may be made within the spirit and scope of the invention.

What is claimed is:

1. In an apparatus for making a non-manual, objective retinal response display, responsive to light stimulus to a human eye; an improved apparatus for providing a selected light stimulus, at selected positions relative to the retinal axis, comprising;
   (a) stimulator means comprising means to supply, on command, a selected one, of a selected plurality of possible beams of light, each positioned so as to enter the lens of an eye of a patient positioned on the axis of said stimulator, at a difficult selected angle to the axis of said stimulator; and means to position the eye of a patient on the axis of said stimulator means;
   (b) machine readable spot control memory means for storing in selected order each of the position parameters of said selected plurality of beams of light; and
   (c) in which said selected beams of light are produced by means of small reflecting surfaces positioned at selected locations on the surface of said stimulator, and a focused beam of light reflected from a small mirror near the axis of said stimulator adapted to be rotated selectively about two perpendicular axes.

2. The apparatus as in claim 1 including display/record means for displaying the position parameters of said selected beam of light.

3. The apparatus as in claim 1 including;
   (a) eye fixation monitor means, and means to direct the optical axis of said fixation monitor means to a selected point on said eye of said patient;
   (b) output means from said fixation monitor means for providing;
      (1) a first electrical signal responsive to the movement of said eye in the X direction;
      (2) a second electrical signal responsive to the movement of said eye in the Y direction.

4. The apparatus as in claim 3 including differential positioning control means, responsive to said machine readable spot control memory means, for supplying to said selector means, a modified position parameter signal, comprising the sum of said recorded selected position parameter from said memory, plus said first and second electrical signals; whereby the actual angle of approach of said selected beam of light to the axis of said eye, will be the same as that which would be supplied by said selected position parameter, if the eye had not moved.

5. The apparatus as in claim 1 including means to modulate said selected one of said selected plurality of beams of light.

6. The apparatus as in claim 5 in which said modulation is amplitude modulation at a constant frequency; and including means to record said constant frequency.

7. The apparatus as in claim 5 in which said modulation is amplitude modulation at a variable frequency; and including means to record said variable frequency.

8. The apparatus as in claim 2 including:
   (a) electrode means attached to the skin of said patient at a selected position; whereby a third electrical signal will be produced which is responsive to the passage of said selected beam of light to a selected portion of the retina of said eye of said patient; and
   (b) means to utilize said third electrical signal.

9. The apparatus as in claim 8 in which said means to utilize includes means to determine the amplitude of said third electrical signal.

10. The apparatus as in claim 8 in which said means to utilize comprises means to digitize and store said third electrical signal.

11. The apparatus as in claim 8 in which said means to utilize comprises means to display/record said third signal in association with said position parameters of said selected beam of light.

12. The apparatus as in claim 8 in which said electrode means is attached to the skin below the lower lid of the eye; whereby said third electrical signal is the electro-retinogram (ERG) of the eye.

13. The apparatus as in claim 8 in which said electrode is attached to the skin behind the lower part of the ear; whereby said third electrical signal is the visual evoked response (VER) of the eye.

14. The apparatus as in claim 8 in which said electrode is attached to the scalp; whereby said third electrical signal is an EEG.

15. The apparatus as in claim 1 in which said focused beam of light comprises a laser beam of selected frequency.

* * * * *